(12) United States Patent
Mori

(10) Patent No.: US 6,342,620 B1
(45) Date of Patent: Jan. 29, 2002

(54) PROCESS FOR PRODUCING PHENYL ESTER

(75) Inventor: Yoshihiko Mori, Kuwana (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 09/537,681

(22) Filed: Mar. 29, 2000

(30) Foreign Application Priority Data

Mar. 31, 1999 (JP) .......................................... 11-091438

(51) Int. Cl.⁷ .............................................. C07C 57/00
(52) U.S. Cl. ........................ 554/134; 554/135; 554/162; 560/131; 562/408
(58) Field of Search ................................ 554/134, 124, 554/163, 165, 135; 560/674, 336, 131; 562/408

(56) References Cited

U.S. PATENT DOCUMENTS 3,642,873 A * 2/1972 Hornig et al. ............... 260/479
3,959,354 A * 5/1976 Onada et al. ............... 260/479

FOREIGN PATENT DOCUMENTS

| | | |
|---|---|---|
| JP | B-71033024 | 9/1971 |
| JP | A-48004439 | 1/1973 |
| JP | B-73018219 | 6/1973 |
| JP | B-75034544 | 11/1975 |
| JP | B-75034548 | 11/1975 |
| JP | A-52027089 | 3/1977 |
| JP | A-48014639 | 4/1980 |
| JP | B-81021463 | 5/1981 |
| JP | A-61200944 | 9/1986 |
| JP | A-61212527 | 9/1986 |
| JP | A-63174950 | 7/1988 |
| JP | A-1290652 | 11/1989 |
| JP | A-1301644 | 12/1989 |
| JP | A-1301645 | 12/1989 |
| JP | A-60246344 | 4/1990 |

* cited by examiner

*Primary Examiner*—Deborah D. Carr
(74) *Attorney, Agent, or Firm*—Sughrue Mion, PLLC

(57) ABSTRACT

A phenyl carboxylate is produced by allowing benzene, a carboxylic acid and molecular oxygen to react with each other in the coexistence of a palladium catalyst with at least one additive selected from alcohols, aldehydes, cyclic hydrocarbons and formic acid. By using the additive, the reduction of catalytic activity of the palladium catalyst with time is minimized.

11 Claims, No Drawings

PROCESS FOR PRODUCING PHENYL ESTER

BACKGROUND OF THE INVENTION (1) Field of the Invention

This invention relates to a process for producing a phenyl ester by allowing benzene, a carboxylic acid and a molecular oxygen to react with each other in the presence of a palladium catalyst.

(2) Description of the Related Art

A process for producing a phenyl ester by allowing benzene, a carboxylic acid and molecular oxygen to react with each other in the presence of a catalyst is well known. Proposals have been made wherein the reaction is conducted in the vapor phase or liquid phase using a noble metal catalyst. Palladium is most popularly used as the main ingredient of the noble catalyst, and some proposals also have been made wherein a co-catalyst comprising a metal, which exhibits by itself no catalytic activity for the specified reaction, is used in combination with the noble catalyst.

For example, a process using a palladium or platinum catalyst optionally combined with gold, silver, copper, iron or manganese is described in Japanese Examined Patent Publication (herein abbreviated to "JP-B") S46-33024, a process using a combination of a palladium or platinum catalyst with bismuth or tellurium is described in JP-B S48-18219, and a process using a combination of a palladium catalyst with a compound comprising a metal selected from cadmium, zinc, uranium, tin, lead, antimony, bismuth, tellurium and thallium, and nitric acid is described in JP-B S55-15455.

Further, as examples of the process using a metal compound catalyst, there can be mentioned a process using a catalyst comprising a combination of an oxide, a hydroxide, an acetate or a nitrate of platinum, palladium, rhodium, ruthenium, iridium or osmium with an alkali metal nitrate (JP-B S50-34544), a process using a combination of metallic palladium or a palladium compound with nitric acid, nitrous acid or metal salts of these acids, and a metal carboxylate (Japanese Unexamined Patent Publication (hereinafter abbreviated to "JP-A") S48-4439, and a process using a combination of palladium acetate with antimony acetate, and at least one metal acetate, the metal of which is selected from chromium, nickel, manganese and iron (JP-B H2-13653).

The processes for allowing benzene, a carboxylic acid and molecular oxygen to react with each other in the liquid phase using a palladium catalyst or a palladium compound catalyst to produce a phenyl ester have a problem such that palladium metal is dissolved in the raw material liquid, and the catalytic activity is reduced with time. Palladium is expensive and thus the above processes are costly. If a step of recovering palladium is conducted, the production processes become complicated. Further, the operation of compensating the catalytic activity decreasing with time is troublesome and not advantageous from an industrial point of view.

In a process using a metal salt catalyst soluble in a reaction liquid, a step of recovering the metal salt must be conducted. Further, a problem arises such that, for example, a palladium salt is used, palladium metal is liable to be deposited on the inner wall of a reactor during the reaction, and this also leads to reduction of catalytic activity with time and loss of palladium.

A process comprising a liquid phase reaction using as a catalyst a combination of palladium with bismuth or lead wherein a soluble bismuth compound or a soluble lead compound is additionally incorporated in the reaction system is described in JP-A S63-174950. In this process, the soluble bismuth or lead compound prevents dissolution of metallic bismuth or lead supported by the palladium catalyst, and thus, dissolution of the main catalyst ingredient, i.e., palladium can be suppressed and the reduction with time of catalytic activity can be minimized. This process has a problem such that the amount of the soluble bismuth or lead compound incorporated is large, and the soluble compound must be recovered as a crystal at the step of separating and purifying a phenyl ester, which leads to complication of the production process.

SUMMARY OF THE INVENTION

In view of the foregoing prior art, an object of the invention is to provide a process for producing a phenyl ester by allowing benzene, a carboxylic acid and molecular oxygen to react with each other in the presence of a palladium catalyst to produce a phenyl ester, wherein the undesirable dissolution of palladium is minimized and the phenyl ester can be produced under stable conditions.

In accordance with the present invention, there is provided an improvement in a process for producing a phenyl ester comprising allowing benzene, a carboxylic acid and molecular oxygen to react with each other in the presence of a palladium catalyst to produce a phenyl ester, said improvement comprising conducting the reaction in the co-presence of at least one compound selected from the group consisting of alcohols, aldehydes, cyclic hydrocarbons and formic acid.

DETAILED DESCRIPTION OF THE PREFERRED EMBODIMENTS

As the palladium catalyst, known palladium catalysts can be used in the invention. The palladium catalyst contains palladium as the main catalyst ingredient. A co-catalyst may be used in combination with the palladium catalyst. The co-catalyst used includes, for example, metals such as gold, silver, copper, iron, manganese, cadmium, zinc, uranium, tin, thallium, lead, bismuth, antimony and tellurium, and compounds thereof. The metal compounds include, for example, oxides, hydroxides, nitrates, sulfates, carbonates, halides, oxyhalides, sulfides, organic carboxylates such as acetates, oxalates, naphthenates and stearates, and organic compounds. The amount of the co-catalyst is not particularly limited provided that a catalyst activity-enhancing effect is obtained. Usually the ratio of palladium to the co-catalyst metal is in the range of 1/0.01 to 1/20 by mole, and preferably 1/0.02 to 1/10 by mole.

The palladium raw material used is not particularly limited, and includes palladium metal and palladium compounds such as, for example, ammonium hexachloropalladate, potassium hexachloropalladate, sodium hexachloropalladate, ammonium tetrachloropalladate, potassium tetrachloropalladate, sodium tetrachloropalladate, potassium tetrabromopalladate, palladium oxide, palladium chloride, palladium bromide, palladium iodide, palladium nitrate, palladium sulfate, palladium acetate, potassium dinitrosulfite-palladate, chlorocarbonyl palladium, dinitrodiamminepalladium, tetraamminepalladium chloride, tetraamminepalladium nitrate, cis-diamminedichloropalladium, trans-diamminedichloropalladium, dichloro(ethylenediamine)palladium, potassium tetracyanopalladate and acetylacetonatopalladium.

The palladium catalyst is preferably used in a state supported by a support which is inactive itself to the specified reaction. As preferable examples of the support, active carbon and silica can be mentioned. In consideration of the catalytic activity and cost, the amount of palladium is usually in the range of 0.01 to 10% by weight, preferably 0.1 to 5% by weight, based on the weight of the support.

The procedure by which the catalyst supported on a support is prepared is not particularly limited, and a conventional procedure for supporting a catalytically active ingredient on a support can be employed. For example, an impregnation, ion exchange, deposition or kneading procedure can be adopted.

When a supported catalyst including a co-catalyst is prepared by an impregnation procedure, a palladium raw material and a co-catalyst raw material can be simultaneously dissolved or dispersed in a liquid medium and a support is impregnated with the solution or dispersion. Alternatively, one of a palladium raw material and a co-catalyst raw material can be dissolved or dispersed in a liquid medium and a support is impregnated with the solution or dispersion, and then, the support is similarly impregnated with the other of the raw materials.

The as-impregnated support by an impregnation or ion-exchange procedure is subjected to conventional operations such as decantation, filtration, heating or vacuum-heating to remove the liquid medium. Then the liquid-removed support may be dried by heating or under a reduced pressure.

The dried catalyst supported on a support is subjected to a reduction treatment to activate palladium. Prior to the reduction treatment, the dried catalyst may be calcined. The calcination is carried out usually at a temperature of 200 to 700° C. in an oxygen-containing atmosphere such as oxygen, air or a mixture of oxygen with nitrogen, helium or argon.

The reduction treatment can be carried out by a conventional procedure. For example, a vapor phase reduction procedure using a reducing agent such as hydrogen, carbon monoxide, ethylene or methanol, or a liquid phase reduction procedure using a reducing agent such as hydrazine hydrate, formalin or formic acid. The vapor phase reduction treatment is carried out usually at a temperature of 100 to 700° C., preferably 200 to 600° C.

In the process of the invention, the reaction of benzene, a carboxylic acid and molecular oxygen to produce a phenyl ester is carried out under the coexistence of a palladium catalyst with an additive selected from alcohols, aldehydes, cyclic hydrocarbons and formic acid. By using the additive, the undesirable dissolution of palladium in the reaction system is suppressed and the reduction of catalytic activity with time can be minimized. Consequently, the reaction can be continued under stable conditions.

The reason for the fact that palladium is dissolved in the reaction system is not clear, but it is presumed that palladium is oxidized during the reaction and finally dissolved in the form of a palladium salt. The function of the additive also is not clear, but it is presumed that the oxidation of palladium is hindered thereby and thus palladium is kept in a metallic state without dissolution into the reaction system.

As specific examples of the alcohols, there can be mentioned those which have 1 to 10 carbon atoms such as methanol, ethanol, 1-propanol, 2-propanol, 1-butanol, 2-butanol, isobutanol, 1-pentanol, 2-pentanol, 3-pentanol, 2-methyl-1-butanol, 2-methyl-2-butanol, 3-methyl-1-butanol, 3-methyl-2-butanol, amyl alcohol, 1-hexanol, 2-hexanol, 3-hexanol, 2-methyl-1-pentanol, 2-methyl-2-pentanol, 2,2-dimethyl-1-butanol, 3,3-dimethyl-1-butanol, 3,3-dimethyl-2-butanol, cyclohexanol, benzyl alcohol, heptanol, 1-octanol, 2-methylheptanol, 2-ethylhexanol, 1-nonanol, isononyl alcohol and 1-decanol. Of these, ethanol is preferable.

As specific examples of the aldehydes, there can be mentioned those which have 1 to 10 carbon atoms such as formaldehyde, acetaldehyde, propionaldehyde, butyraldehyde, isobutyraldehyde, 2-methylbutyraldehyde, valeraldehyde, isovaleraldehyde, pivalaldehyde, capronaldehyde, 2-ethylbutyraldehyde, 2-methyl-n-valeraldehyde, heptylaldehyde, benzaldehyde, salicylaldehyde, caprylaldehyde, 2-ethylhexylaldehyde, toluylaldehyde, phthalaldehyde, pelargonaldehyde and caprinaldehyde. Of these, acetaldehyde is most preferable.

As specific examples of the cyclic hydrocarbons, there can be mentioned those which have 3 to 10 carbon atoms such as cyclohexane, cyclohexene, cyclohexadiene and tetrahydronaphthalene. Of these, cyclohexene is preferable.

The amount of the additive used varies depending upon the kind of additive and the manner in which a phenyl ester is prepared, and is not particularly limited. Usually the amount of the additive is in the range of 0.00001 to 10 moles per mole of benzene.

The carboxylic acid to be reacted with benzene and molecular oxygen includes those which have not larger than 10 carbon atoms. As specific examples of the carboxylic acid, there can be mentioned monocarboxylic acids such as acetic acid, propionic acid and butyric acid, and dicarboxylic acids such as adipic acid. Lower monocarboxylic acids having 2 to 6 carbon atoms such as acetic acid and propionic acid are preferable.

The amount of the carboxylic acid is not particularly limited, but is preferably in the range of 0.1 to 100 moles per mole of benzene.

Benzene, carboxylic acid and molecular oxygen are allowed to react with each other in the presence of the palladium catalyst in the liquid phase. By the term "liquid phase" used herein, we mean that the surface of the catalyst is covered with a reaction liquid and the reaction procedure is not particularly limited. For example, a fixed bed flow-through type reactor, a fluidized bed flow-through type reactor, a batch reactor and suspension bed reactor can be used.

The amount of the catalyst used varies depending upon the particular reaction procedure and is not particularly limited. For cost consideration, in the case where a fixed bed type reactor is used, the amount of the catalyst is usually in the range of 0.1 to 50 $h^{-1}$, preferably 0.1 to 30 $h^{-1}$, as liquid hourly space velocity (LHSV), i.e., as the total feed volume rate of benzene plus carboxylic acid per unit volume of the catalyst and per unit time (hr). In the case where a suspension bed type reactor is used, the concentration of the catalyst is preferably in the range of 0.05 to 30% by weight based on the total weight of benzene and carboxylic acid.

The reaction temperature is usually in the range of 100 to 300° C., preferably 100 to 250° C. The reaction pressure is such that the catalyst surface is covered with a liquid raw material at the reaction temperature, and is preferably in the range of 10 to 100 atmospheric pressure.

The molecular oxygen used as an oxidizing agent in the process of the invention may be diluted with an inert gas such as nitrogen, helium or argon, and air may be used. The optimum amount of oxygen varies depending upon the reaction temperature, the amount of catalyst and other factors, and is not particularly limited provided that the gas composition flowing through a catalyst-packed site is out of the explosive range.

The reaction time varied depending upon the reaction temperature and pressure, the amount of catalyst and the manner in which reaction is performed, and is not particularly limited. For example, when the reaction is performed in a batchwise or semi-batchwise manner, the reaction time is usually at least 0.5 hour. When the reaction is performed in continuous manner using a suspension bed or a fixing bed, the residence time is usually in the range of 0.03 to 10 hours.

The invention will now be described by the following examples that by no means limit the scope of the invention.

Preparation of Catalyst (1)

In 16 g of distilled water, 3.55 g of tartaric acid was dissolved, followed by addition of 0.49 g of antimony oxide. Then 7.27 g of an aqueous 8.26% by weight palladium nitrate solution was added. 20 g of silica ("CARIACT Q-30"™ supplied by Fuji Silysia Chemical Ltd.) was impregnated with the thus-prepared aqueous palladium-containing solution. The mixture was then dried at 50° C. under a reduced pressure, vacuum-dried at 100° C. for 3 hours, calcined at 400° C. in air for 5 hours, and then subjected to reduction treatment by applying hydrogen at 400° C. for 5 hours to give catalyst (1). The amount of palladium supported by silica was 3% by weight based on the weight of silica. The ratio of antimony to palladium was 3/5 by mole.

Preparation of Catalyst (2)

7.27 g of an aqueous 8.26% by weight palladium nitrate solution was weighed. Into this solution, 0.13 g of telluric acid and distilled water were added to a volume of 21 ml. 20 g of silica ("CARIACT Q-30"™ supplied by Fuji Silysia Chemical Ltd.) was impregnated with the thus-prepared aqueous palladium-containing solution. The mixture was then dried at 50° C. under a reduced pressure, vacuum-dried at 100° C. for 3 hours, calcined at 400° C. in air for 5 hours, and then subjected to reduction treatment by applying hydrogen at 400° C. for 5 hours to give catalyst (2). The amount of palladium supported by silica was 3% by weight based on the weight of silica. The ratio of tellurium to palladium was 1/10 by mole.

EXAMPLE 1

A reaction tube having an inner diameter of 13 mm made of SUS 316 was packed with 10 ml of catalyst (1). An equimolar mixed liquid of benzene and acetic acid was continuously supplied into the reaction tube at a rate of 2.2 g/min together with 27 Nml/min of oxygen gas and 183 Nml/min of nitrogen to conduct a reaction. The equimolar benzene/acetic acid mixed liquid had methanol previously incorporated therein in an amount such that the ratio of benzene/acetic acid/methanol was 49/49/2 by mole.

Samples of the reaction mixture were collected for analysis twice, i.e., 5 hours and 50 hours after the commencement of reaction. Each sample was separated into the gaseous component and the liquid component. The two components were analyzed by gas chromatography to determine the yield of phenyl acetate ester. The ratio of $yield_{50hr}/yield_{5hr}$ was determined wherein $yield_{50hr}$ and $yield_{5hr}$ are yields of phenyl acetate as measured on a sample collected 50 hours after the commencement of reaction and a sample collected 5 hours after the commencement of reaction, respectively. The larger the ratio of $yield_{50hr}/yield_{5hr}$, the smaller the reduction of catalytic activity with time.

The amount of palladium dissolved in the reaction mixture during a period of 50 hours from the commencement of reaction was measured by the atomic-absorption spectroscopy. The dissolution % of palladium, i.e., the ratio in % of the amount of palladium dissolved during 50 hours to the amount of palladium initially supported on a support was calculated.

The ratio of $yield_{50hr}/yield_{5hr}$, and the dissolution % of palladium are shown in Table 1.

EXAMPLES 2 TO 6

The procedures described in Example 1 were repeated to produce phenyl acetate wherein ethanol, 2-propanol, 2-butanol, formic acid and cyclohexane were separately used instead of methanol as an additive with all other conditions remaining the same. The results are shown in Table 1.

EXAMPLE 7

The procedures described in Example 1 were repeated to produce phenyl acetate wherein ethanol was used instead of methanol as an additive and the amount of ethanol was such that the ratio of benzene/acetic acid/ethanol in the mixed liquid was 45/45/10 by mole. All other conditions remained the same. The results are shown in Table 1.

EXAMPLE 8

The procedures described in Example 1 were repeated to produce phenyl acetate wherein cyclohexene was used instead of methanol as an additive and the amount of cyclohexene was such that the ratio of benzene/acetic acid/cyclohexene in the mixed liquid was 49.925/49.925/0.15 by mole. All other conditions remained the same. The results are shown in Table 1.

EXAMPLE 9

The procedures described in Example 1 were repeated to produce phenyl acetate wherein cyclohexene was used instead of methanol as an additive and the amount of cyclohexene was such that the ratio of benzene/acetic acid/cyclohexene in the mixed liquid was 49.75/49.75/0.5 by mole. All other conditions remained the same. The results are shown in Table 1.

Comparative Example 1

The procedures described in Example 1 were repeated to produce phenyl acetate wherein methanol as an additive was not used with all other conditions remaining the same. The results are shown in Table 1.

TABLE 1

| Example No. | Additive Kind | Additive Amount (%) | $yield_{50\ hr}/yield_{5\ hr}$ | Pd dissolution (%) |
|---|---|---|---|---|
| Ex. 1 | Methanol | 2 | 0.58 | 1.6 |
| Ex. 2 | Ethanol | 2 | 0.65 | 2.0 |
| Ex. 3 | 2-Propanol | 2 | 0.54 | 2.3 |
| Ex. 4 | 2-Butanol | 2 | 0.53 | 2.9 |
| Ex. 5 | Formic acid | 2 | 0.75 | 0.2 |
| Ex. 6 | Cyclohexane | 2 | 0.37 | 4.8 |
| Ex. 7 | Ethanol | 10 | 0.91 | 0.2 |
| Ex. 8 | Cyclohexene | 0.15 | 0.33 | 2.2 |
| Ex. 9 | Cyclohexene | 0.5 | 0.55 | 1.1 |
| Co. Ex. 1 | — | 0 | 0.30 | 6.4 |

EXAMPLE 10

The procedures described in Example 1 were repeated to produce phenyl acetate wherein catalyst (2) was used instead of catalyst (1), ethanol was used instead of methanol as an additive and the amount of ethanol was such that the ratio of benzene/acetic acid/ethanol in the mixed liquid was 49/49/2 by mole. All other conditions remained the same. The results are shown in Table 2.

EXAMPLE 11

The procedures described in Example 10 were repeated to produce phenyl acetate wherein the composition of the mixed liquid was changed so that the ratio of benzene/acetic acid/ethanol was 45/45/10 by mole. All other conditions remained the same. The results are shown in Table 2.

EXAMPLE 12

The procedures described in Example 10 were repeated to produce phenyl acetate wherein cyclohexene was used instead of ethanol as an additive and the amount of cyclohexene was such that the ratio of benzene/acetic acid/cyclohexene in the mixed liquid was 49.875/49.875/0.25 by mole. All other conditions remained the same. The results are shown in Table 2.

EXAMPLE 13

The procedures described in Example 10 were repeated to produce phenyl acetate wherein cyclohexene was used instead of ethanol as an additive and the amount of cyclohexene was such that the ratio of benzene/acetic acid/cyclohexene in the mixed liquid was 49.75/49.75/0.5 by mole. All other conditions remained the same. The results are shown in Table 2.

EXAMPLE 14

The procedures described in Example 10 were repeated to produce phenyl acetate wherein acetaldehyde was used instead of ethanol as an additive and the amount of acetaldehyde was such that the ratio of benzene/acetic acid/acetaldehyde in the mixed liquid was 49.75/49.75/0.5 by mole. All other conditions remained the same. The results are shown in Table 2.

Comparative Example 2

The procedures described in Example 10 were repeated to produce phenyl acetate wherein ethanol as an additive was not used with all other conditions remaining the same. The results are shown in Table 2.

TABLE 2

| Example | Additive | | $yield_{50\,hr}/$ | Pd dissolution |
|---|---|---|---|---|
| No. | Kind | Amount (%) | $yield_{5\,hr}$ | (%) |
| Ex. 10 | Eethanol | 2 | 0.62 | 0.4 |
| Ex. 11 | Ethanol | 10 | 0.68 | 0.1 |
| Ex. 12 | Cyclohexene | 0.25 | 0.58 | 0.1 |

TABLE 2-continued

| Example | Additive | | $yield_{50\,hr}/$ | Pd dissolution |
|---|---|---|---|---|
| No. | Kind | Amount (%) | $yield_{5\,hr}$ | (%) |
| Ex. 13 | Cyclohexene | 0.5 | 0.60 | 0.0 |
| Ex. 14 | Acetaldehyde | 0.5 | 0.64 | 0.5 |
| Co. Ex. 2 | — | 0 | 0.54 | 1.2 |

What is claimed is:

1. An improvement in a process for producing a phenyl ester comprising allowing benzene, a carboxylic acid having at least two carbon atoms and molecular oxygen to react with each other in the presence of a palladium catalyst to produce a phenyl ester, said improvement comprising conducting the reaction in the liquid phase and in the co-presence of at least one compound selected from the group consisting of alcohols, aldehydes, cyclic hydrocarbons and formic acid.

2. The process according to claim 1, wherein the alcohols are alcohols having 1 to 10 carbon atoms.

3. The process according to claim 1, wherein the aldehydes are aldehydes having 1 to 10 carbon atoms.

4. The process according to claim 1, wherein the cyclic hydrocarbons are cyclic hydrocarbons having 3 to 10 carbon atoms.

5. The process according to claim 4, wherein the cyclic hydrocarbon is selected from the group consisting of cyclohexane, cyclohexene, cyclohexadiene and tetrahydronaphthalene.

6. The process according to claim 1, wherein the carboxylic acid is a carboxylic acid having 2 to 10 carbon atoms.

7. The process according to claim 1 wherein a mixed liquid comprising benzene and the carboxylic acid and having incorporated therein at least one compound selected from the group consisting of alcohols, aldehydes, cyclic hydrocarbons and formic acid, and molecular oxygen, are brought into contact with the palladium catalyst.

8. The process according to claim 1, wherein the liquid phase reaction is conducted in the co-presence of at least one compound selected from the group consisting of alcohols and aldehydes.

9. The process according to claim 1, wherein the liquid phase reaction is conducted in the co-presence of at least one cyclic hydrocarbon.

10. The process according to claim 1, wherein the liquid phase reaction is conducted in the co-presence of formic acid.

11. The process according to claim 1, wherein the at least one compound selected from the group consisting of alcohols, aldehydes, cyclic hydrocarbons and formic acid is present in an amount of 0.00001 to 10 mols per mole of benzene, whereby the undesirable dissolution of palladium is minimized.

* * * * *